United States Patent [19]

Mattson

[11] Patent Number: 5,127,915
[45] Date of Patent: Jul. 7, 1992

[54] SURGICAL INSTRUMENT FOR SEVERING AND CLAMPING AN UMBILICAL CORD

[76] Inventor: Philip D. Mattson, 1776 Plantation Way, El Cajon, Calif. 92020

[21] Appl. No.: 222,281

[22] Filed: Jul. 20, 1988

Related U.S. Application Data

[63] Continuation of Ser. No. 882,984, filed as PCT/US85/02118, Oct. 28, 1985, abandoned, which is a continuation-in-part of Ser. No. 665,723, Oct. 29, 1984, Pat. No. 4,648,401.

[51] Int. Cl.⁵ ............................................. A61B 17/08
[52] U.S. Cl. ..................................... 606/120; 606/157
[58] Field of Search ............... 128/305, 346, 326, 325, 128/318, 321; 604/22; 606/120, 157, 158

[56] References Cited

U.S. PATENT DOCUMENTS

| | | | |
|---|---|---|---|
| 2,384,697 | 9/1945 | Riccardi | 128/346 |
| 2,524,337 | 10/1950 | Whittaker | 128/346 X |
| 3,106,919 | 10/1963 | Churchville | 128/305 X |
| 3,581,551 | 6/1971 | Wilkinson | 128/325 X |
| 3,631,858 | 1/1972 | Ersek | 128/318 |
| 3,776,925 | 10/1973 | Rubricius . | |
| 4,026,294 | 5/1977 | Mattler | 128/346 |
| 4,193,174 | 3/1980 | Stephens . | |
| 4,337,774 | 7/1982 | Perlin . | |
| 4,345,600 | 8/1982 | Rothfuss . | |
| 4,346,869 | 8/1982 | MacNeill . | |
| 4,387,489 | 6/1983 | Dudek . | |
| 4,390,019 | 6/1983 | LeVeen . | |
| 4,434,795 | 3/1984 | Mericle | 128/346 X |
| 4,453,295 | 6/1984 | Laszczower . | |
| 4,478,218 | 10/1984 | Mericle | 128/325 |
| 4,492,232 | 1/1985 | Green | 128/325 |
| 4,572,181 | 2/1986 | Mattler . | |
| 4,600,007 | 7/1986 | Lahodny et al. . | |

FOREIGN PATENT DOCUMENTS

| | | | |
|---|---|---|---|
| 2525650 | 12/1976 | Fed. Rep. of Germany | 128/346 |
| 392802 | 5/1933 | United Kingdom | 128/325 |
| 934296 | 8/1963 | United Kingdom | 128/318 |

Primary Examiner—Michael H. Thaler
Attorney, Agent, or Firm—Beveridge, DeGrandi & Weilacher

[57] ABSTRACT

A surgical instrument for severing an umbilical cord while simultaneously applying a single umbilical cord clamp and compressing the placental (maternal) end of the cord is discussed. The instument allows release of the hemostat on the maternal end of the umbilical cord immediately after severence of the cord for enabling collection of a blood specimen for a fetal thyroid screen test to avoid discomforting the infant by obtaining the specimen directly from the infant. The instrument includes upper and lower clamping jaws having arranged thereon means for detachably holding an umbilical cord clamp, a blade assembly, and upper and lower hemostat surfaces adapted to compress the umbilical cord when the upper and lower clamping jaws are closed.

Further in accordance with the present invention, a generally V-shaped umbilical cord clamp having a pair of arms joined together at an integral hinge and head portions including locking means at the free ends thereof is provided with a channel or opening extending generally diagonally through at least one of the head portions, such channel communicating with the locking means in the head portion to release such locking means when the arms are locked together in clamping position.

11 Claims, 5 Drawing Sheets

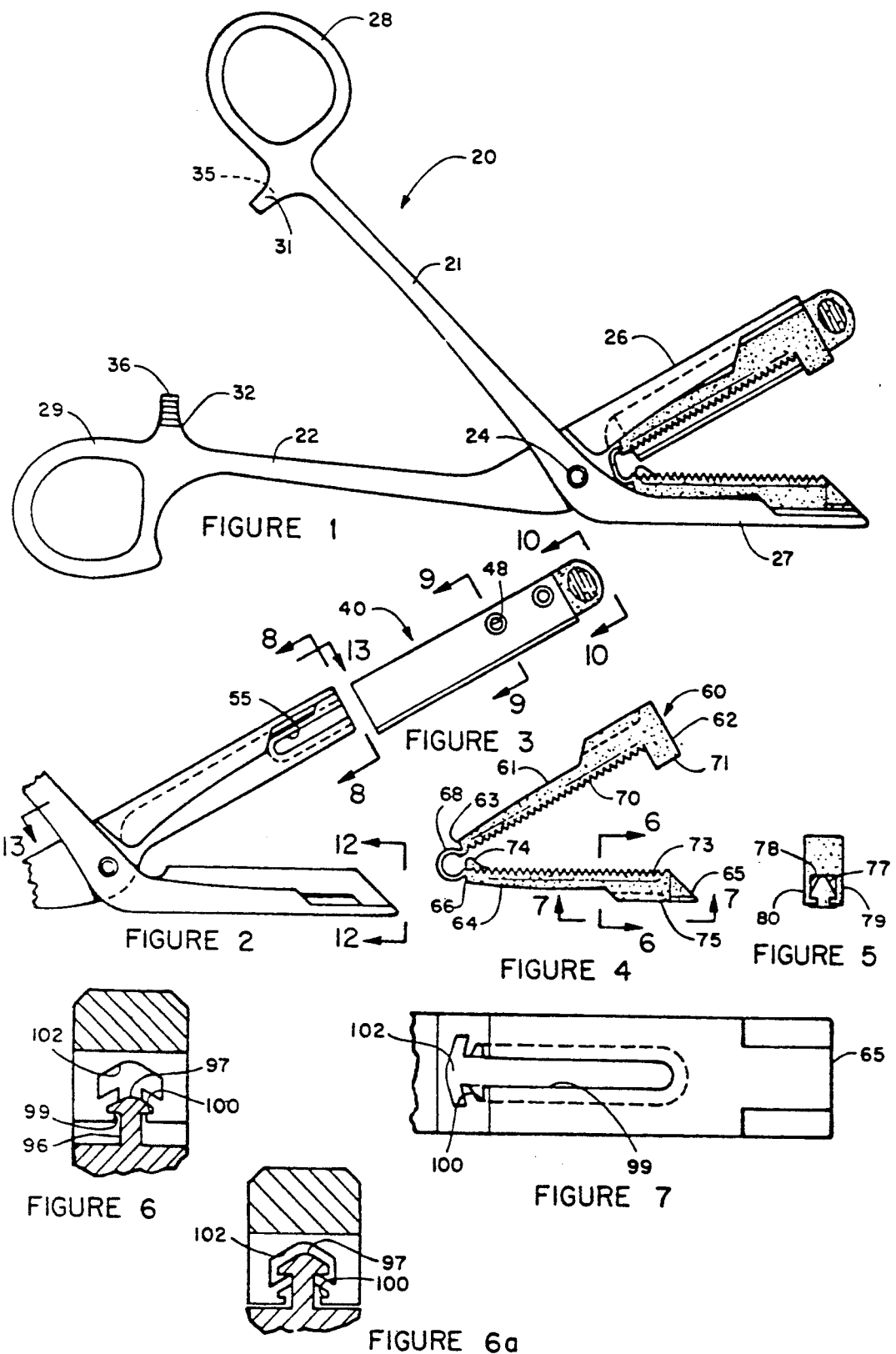

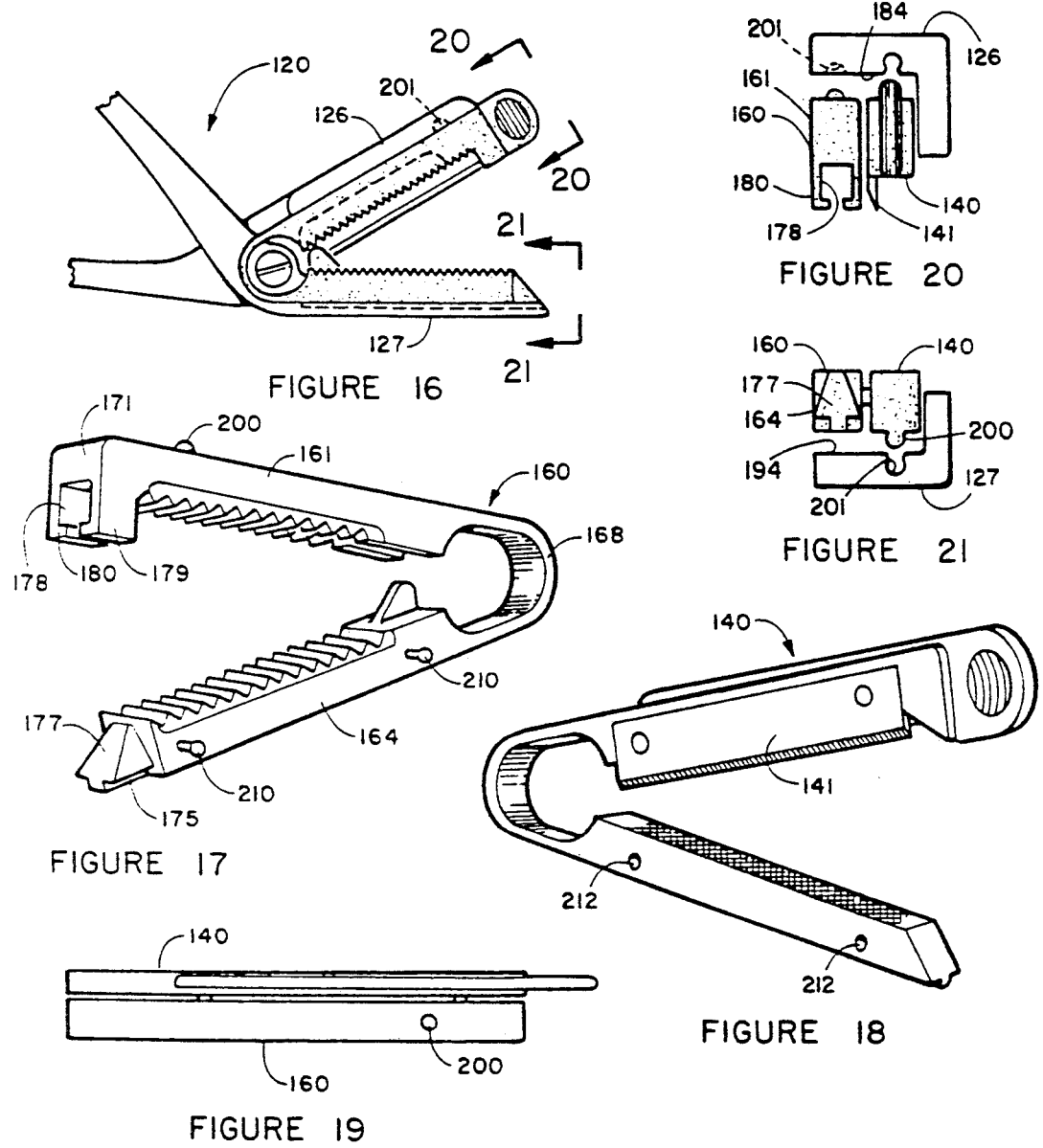

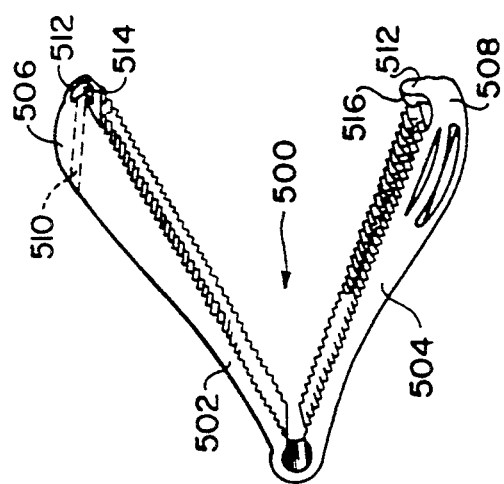
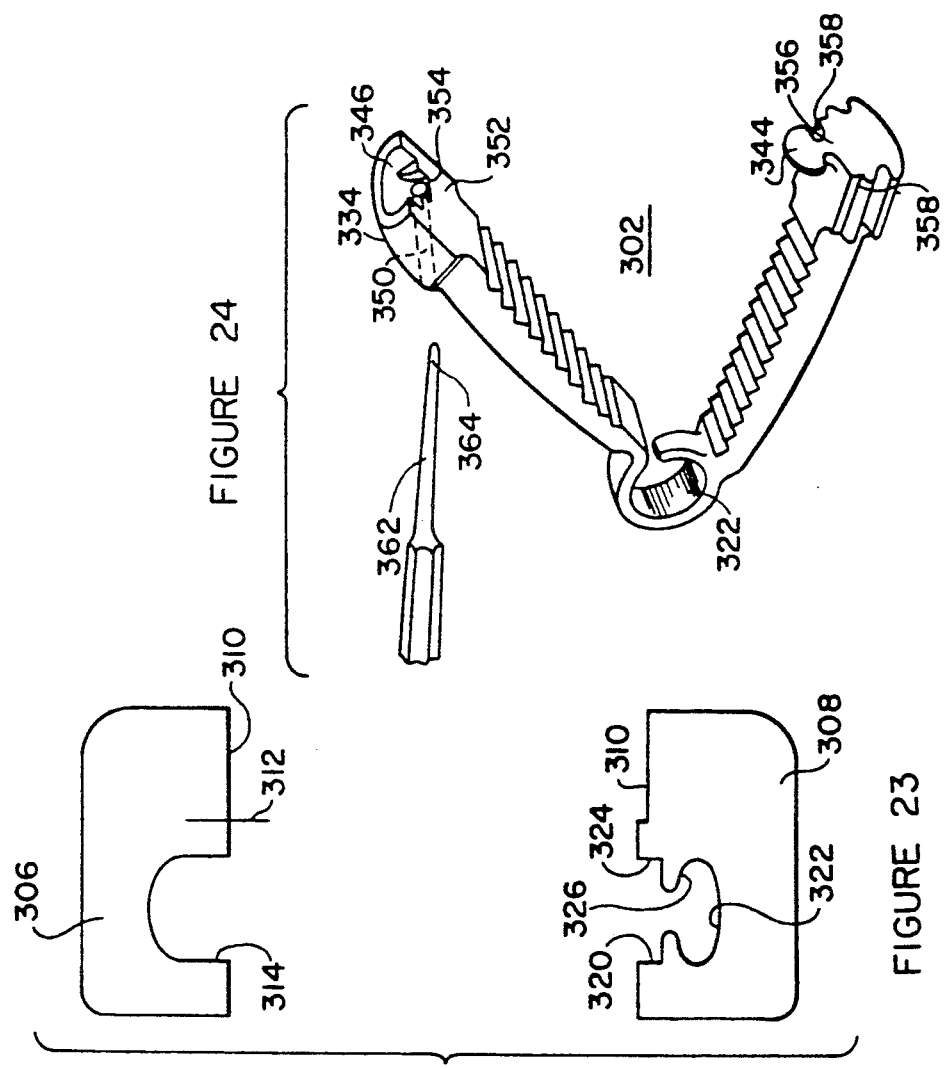
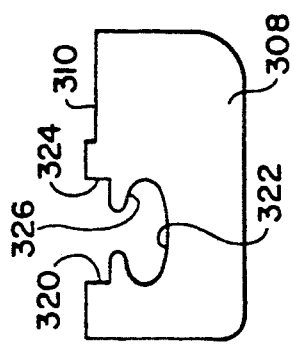

SURGICAL INSTRUMENT FOR SEVERING AND CLAMPING AN UMBILICAL CORD

This application is a continuation of application Ser. No. 06/882,984, filed as PCT/US25/02118, Oct. 28, 1985, abandoned which is a continuation-in-part of Ser. No. 06/665,723 filed Oct. 29, 1984, now U.S. Pat. No. 4,648,401.

BACKGROUND OF THE INVENTION

The umbilical cord is a rope-like structure which connects the fetus to the placenta. The cord contains two arteries and one vein. The arteries carry blood containing waste products from the fetus to the placenta. The vein carries blood containing oxygen and food substances obtained from the mother's blood back to the fetus.

At the present time, the procedure followed by many obstetricians following the delivery of the baby, is to clamp two separate hemostats on the umbilical cord at spaced positions and use a pair of scissors to sever the umbilical cord. Subsequently an umbilical cord clamp is manually applied to the cord adjacent the baby's navel and a second cutting of the redundant portion of the cord between the clamp and the hemostat is performed.

In recent years various umbilical cord clamping assemblies have been designed to improve and expedite the process of severing the umbilical cord and properly clamping it. An example is in U.S. Pat. No. 3,150,666, which shows an instrument for clamping one end of the umbilical cord and then applying an elastic band around the cord. Another instrument, disclosed in U.S. Pat. No. 3,166,071, provides means for simultaneously applying two spaced-apart umbilical cord clamps and severing the umbilical cord therebetween. Likewise, U.S. Pat. No. 4,428,374 shows an umbilical cord clamping assembly for simultaneously applying a pair of spaced-apart umbilical clamps, connected by a connecting member. As the clamping tool applies the clamps, it severs both the cord and the connecting member between the clamps.

U.S. Pat. No. 4,026,294 presents another example of a clamping and cutting surgical instrument wherein two umbilical clamps are applied to the cord after which the cord is severed. U.S. Pat. No. 3,631,858 shows another simultaneously clamping and severing device including clamping jaws and cutting jaws held together in side-by-side relationship by a web. As the cord is severed and clamped, the web is also severed so that the cutting jaws can be removed while the clamp remains on the cord.

Prior art surgical instruments for clamping and severing an umbilical cord have not gained widespread acceptance. Unfortunately, the few seconds wasted by present procedures for severing and clamping the umbilical cord may be the difference between a routine birth or one complicated by serious lung problems in the infant.

It is thus an object of the invention to provide a novel surgical instrument for clamping and severing an umbilical cord, the parts of which are easily manufactured and assembled.

It is also an object of the invention to provide a novel surgical instrument for clamping and severing an umbilical cord that will simplify and speed up the operation.

It is another object of the invention to provide a novel surgical instrument for clamping and severing an umbilical cord wherein the instrument applies a single umbilical cord clamp, severs the umbilical cord, and maintains a hemostat on the maternal end of the cord.

It is still another object of the invention to provide a novel surgical instrument for clamping and severing an umbilical cord wherein the umbilical cord clamp is detached from the instrument without opening its clamping jaws.

It is a further object of the invention to provide a novel surgical instrument for clamping and severing an umbilical cord which includes a single-use, disposable blade assembly.

It is still another object of this invention to provide an umbilical cord clamp which can be readily detached from the umbilical cord portion attached to the infant without the need for severing the clamp at its hinge portion.

SUMMARY

Applicant's novel surgical instrument for clamping and severing an umbilical cord provides many benefits such as hastening the availability of the newborn child for inspection to reduce the risk of fetal aspiration. A major concern is merconium (fetal bowel movement) aspiration leading to pulmonary complications. Maternal blood and amniotic fluid aspiration are of a lesser concern. It is believed that the known procedures requiring 6-7 seconds for severing the cord could be reduced to 2-3 seconds with the present invention. Thus the infant's attendant who is to perform direct tracheal suctioning, is provided with an opportunity to suction the infant's air passages possibly before the infant's first breath or, at least before its second breath, to prevent material from reaching far into the bronchi.

Applicant's novel surgical instrument and the manner in which it is used shall now be described. The surgical instrument initially would be loaded with an umbilical cord clamp and a new blade assembly. As the obstetrician delivers the baby, he would cradle the baby in one arm while simultaneously picking up the loaded instrument with the other arm. The upper and lower jaws of the instrument would be placed in contact with the baby's umbilical cord adjacent its navel and a clamping action would be performed. At the completion of the clamping stroke, the umbilical cord clamp remains locked on the baby's umbilical cord adjacent its navel while the remainder of the umbilical cord is severed therefrom. Particular movement of the surgical instrument, as by hand, detaches the umbilical cord clamp from the surgical instrument without opening the instrument's clamping jaws, while the hemostat surfaces of the surgical instrument maintain a tight clamping action on the maternal end of the umbilical cord. After this clamping and severing procedure, the baby would be handed to the infant's attendant for immediate, direct trachael suctioning. Clamping by the hemostat surfaces on the maternal end of the cord could then be released just long enough to collect a blood specimen for a fetal thyroid screen test. The hemostat surfaces would then be reclamped with the redundant cord rolled about the instrument with gentle traction applied to enhance the delivery of the placenta from the mother.

Thus the surgical instrument of the present invention replaces the two hemostats and scissors previously needed. Further, since the instrument of the present invention requires only one severence of the cord, the risk of innoculating exposed blood vessels in the cord with infected amniotic fluid is reduced. Finally, since the instrument in accordance with the present invention provides means to sever and clamp the cord in very close proximity to the infant, it obviates conventional procedures requiring a scrub nurse to hand sterile scissors to an often ungloved attendant to trim and clamp the redundant cord. The use of gloves by an attendant is discouraged because they make it difficult to catch the wet baby and to perform trachael suctioning on the baby. The use of conventional procedures expose the attendant's hands to blood from the severed cord while performing such trimming and clamping. Obviating such conventional procedures is now especially important in view of the present threat of hepatitis and/or AIDS.

DESCRIPTION OF THE DRAWINGS

FIG. 1 is a side elevational view of a surgical instrument for clamping and severing an umbilical cord in accordance with the present invention;

FIG. 2 is a partial side elevational view of the instrument of FIG. 1 with the blade assembly removed;

FIG. 3 is a side elevational view of a blade assembly suitable for use with the surgical instrument of FIG. 1;

FIG. 4 is a side elevational view of a first embodiment of an umbilical cord clamp in accordance with the present invention;

FIG. 5 is an end elevational view of the umbilical cord clamp of FIG. 4 in its closed position;

FIG. 6 is a cross-sectional view taken along line 6—6 of FIG. 4 illustrating the initial engagement of the lower clamping jaw of the instrument with the clamp;

FIG. 6a is a cross-sectional view taken along line 6—6 of FIG. 4 and illustrates the mating of the lower clamping jaw of the instrument with the clamp once the upper and lower clamping jaws have been closed;

FIG. 7 is a bottom plan view taken along line 7—7 of FIG. 4;

FIG. 16 is a partial side elevational view of a first alternative embodiment of a surgical instrument in accordance with the present invention;

FIG. 17 is a perspective view of a second alternative embodiment of an umbilical cord clamp utilized with the instrument illustrated in FIG. 16;

FIG. 18 is a perspective view of a blade assembly utilized with the instrument illustrated in FIG. 16;

FIG. 19 is a top plan view of the blade assembly illustrated in FIG. 18;

FIG. 20 is an elevational view taken along line 20—20 of FIG. 16;

FIG. 21 is an elevational view taken along line 21—21 of FIG. 16;

FIG. 23 is a front sectional view of the jaws of the instrument of FIG. 22;

FIG. 24 is a perspective view of a third alternative embodiment of an umbilical cord clamp in accordance with the present invention; and FIG. 25 is a perspective view of a fourth alternative embodiment of an umbilical cord clamp having rounded arms and head portions and an opening therethrough in accordance with the present invention.

DESCRIPTION OF THE PREFERRED EMBODIMENT

Figure 8:
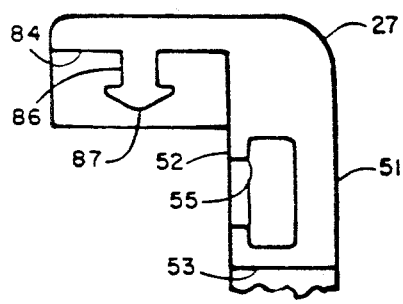
FIG. 8 is an end elevational view taken along line 8—8 of FIG. 2.

A first embodiment of a surgical instrument for severing an umbilical cord will be described with reference to FIGS. 1- 19. The surgical instrument is generally designated by numeral 20. It has a pair of elongated handles 21 and 22 that are pivoted with respect to each other around a pivot pin 24. An upper clamping jaw 26 is formed on the free end of handle 22 and a lower clamping jaw 27 is formed on the free end of handle 21.

Finger gripping members 28 and 29 are formed on the ends of the respective handle members 21 and 22. The length of handles 21,22 in combination with finger gripping members 28,29 provides sufficient leverage to sever the umbilical cord in a single clamping motion. To lock jaws 26 and 27 in place, extensions 31 and 32 are provided. Extensions 31 and 32 have corresponding buttress-teeth 35 and 36, which teeth mate to lock handles 21 and 22 in a particular position.

Surgical instrument 20 may be made of any suitable material, but preferably would be made from stainless steel. A disposable model, however, preferably would be made from a plastic material.

Removable blade assembly 40 is best illustrated in FIGS. 3, and 9-11. Blade assembly 40 has an elongated blade member 41 having a front surface 42, a rear surface 43, and a bottom cutting edge 44. A support member 46 having a T-shaped cross-sectional configuration is secured to the rear surface by means such as rivets 48 shown in FIG. 3. A finger gripping member 49 is formed on one end of support member 46 to aid in removing blade assembly 40 from upper clamping jaw 26. Where surgical instrument 20 is of the disposable type, the blade assembly may be permanently secured to jaw 26 rather than being removable.

Figures 9, 10, 11:
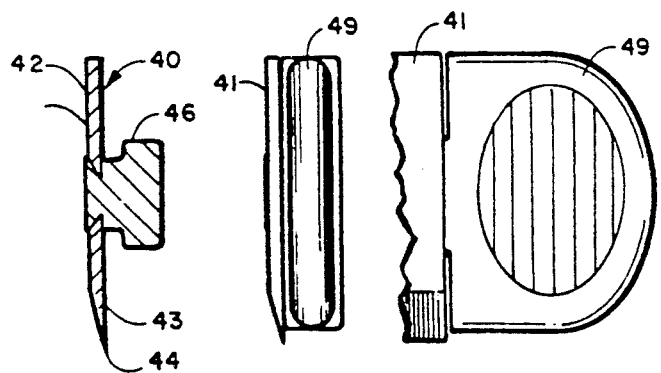
FIG. 9 is a cross-sectional view taken along line 9—9 of FIG. 3.
FIG. 10 is an end elevational view of the blade assembly of FIG. 3.
FIG. 11 is a partial front elevational view of the blade assembly of FIG. 3.

The manner in which blade assembly 40 is supported in upper clamping jaw 26 is best understood by referring to FIGS. 2, 8 and 9. As shown in those figures, upper clamping jaw 26 has an exterior wall surface 51, an interior wall surface 52, and an upper hemostat surface 53. An open ended slot 55 has a T-cross-sectional configuration that matingly receives T-shaped support member 46 on the rear of blade 41. Alternatively, the blade assembly may be supported by the lower clamping jaw in a manner similar to that described above.

Umbilical cord clamp 60, ideally suited for use with surgical instrument 20, is illustrated in FIG. 4. Clamp 60 has an upper arm 61 having a front end 62 and a rear end 63. It also has a lower arm 64 having a front end 65 and a rear end 66. Rear ends 63 and 66 are connected together by integral hinge portion 68. Upper arm 61 also has teeth 70 on its lower surface and a head portion 71. Lower arm 64 has teeth 73 on its top surface and further includes an umbilical cord blocking member 74 and a head portion 75. The manner in which head portion 71 of upper arm 61 and head portion 75 of lower arm 64 clamp together is illustrated in FIG. 5. A tongue portion 77 is formed on head portion 75 and it is clamped into groove 78 by resilient flanges 79 and 80 formed on the bottom of head portion 71.

Upper arm 61 and lower arm 64 have similar corresponding structure for detachably securing or coupling them to the respective upper and lower clamping jaws 26 and 27. FIGS. 6 and 6a along with FIGS. 8 and 12 aid in understanding the detachable securing or coupling of arms 61 and 64 with jaws 26 and 27. As seen in FIG. 8, upper clamping jaw 26 has a channel 84 formed by interior wall surface 52. Upper arm 62 of umbilical clamp 60 nests in channel 84 and attaches to upper jaw 26 by means of neck member 86 and tongue portion 87 that extend into the mating structure, discussed infra, on the top of head portion 71. This mating relationship will be described with respect to the similar mating or coupling structure included in lower clamping jaw 27, as illustrated in FIGS. 6, 6a and 12.

Figure 12:
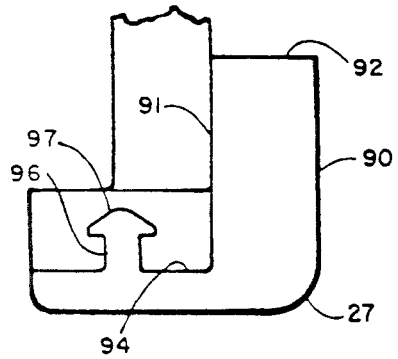
FIG. 12 is an end elevational view taken along line 12—12 of FIG. 2.

As seen from FIG. 12, lower clamping jaw 27 has an exterior surface 90, an interior wall surface 91, and a lower hemostat surface 92. A channel 94 is formed by interior wall surface 91. A neck member 96 extends upwardly from channel 94 and includes a tongue portion 97 on its top end.

FIG. 6 illustrates the initial loaded position of lower arm 64 of umbilical clamp 60 and its manner of attachment to tongue portion 97 of lower clamping jaw 27. Head portion 75 has a primary groove 100 formed in its bottom surface which matingly receives tongue 97 of lower clamping jaw 27. As the upper and lower clamping jaws 26 and 27 are firmly clamped about the umbilical cord, tongue 97 is driven into secondary groove 102. Since the dimensions of secondary groove 102 are larger than those of tongue 97, tongue 97 is freely movable within the constraints of secondary groove 102. Thus surgical instrument 20 may be pulled away from umbilical cord clamp 60 once clamp 60 has been clamped to the new born baby adjacent the navel area.

Figure 13:
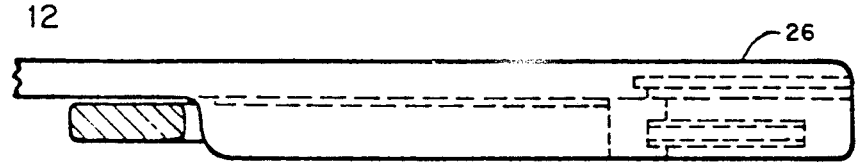
FIG. 13 is a top plan view of the upper clamping jaw of the instrument of FIG. 1 with the top portion of the umbilical cord clamp shown as loaded therein.
Figure 14:
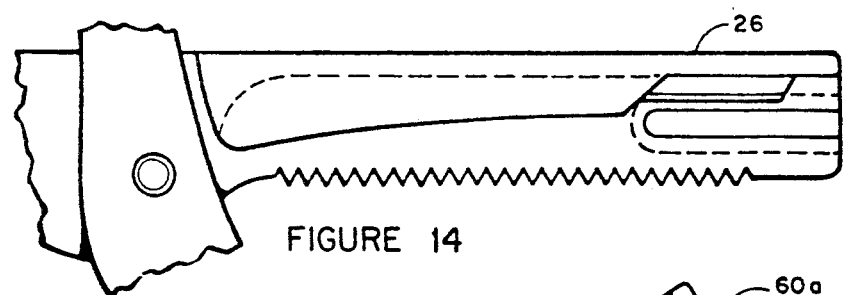
FIG. 14 is a side elevational view of the upper clamping jaw of FIG. 13 with the top arm of the umbilical cord clamp shown as inserted therein.

FIG. 7 is a bottom plan view which further aids in understanding the configuration of primary and secondary grooves 100 and 102 in the bottom of head portion 75. Similar primary and secondary grooves are found in the top surface of head portion 71 of upper arm 61. FIGS. 13 and 14 illustrate clamp 60 attached to the upper clamping jaw 26.

While clamp 60 is securely coupled to both jaw 26 and 27 by means of tongues and primary and secondary grooves as discussed, other coupling arrangements are possible. For example, only one of the opposing jaws and one of the upper and lower arms need include the mating tongue and groove means discussed supra. In such an embodiment, such coupling means could be included on either the upper or the lower jaws and such corresponding coupling means could likewise be included on either the upper or the lower arm.

Figure 15:
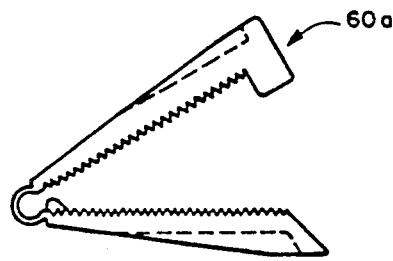
FIG. 15 is a side elevational view of a first alternative embodiment of an umbilical cord clamp in accordance with the present invention.

A first alternative umbilical cord clamp 60a is illustrated in FIG. 15 and has longer primary and secondary grooves shown in broken lines as extending along the respective upper and lower arms.

A modified surgical instrument 120 is illustrated in FIG. 16. Instrument 120 utilizes an umbilical cord clamp 160 and a blade assembly 140, shown respectively in FIGS. 17 and 18, and shown as assembled in the top plan view of FIG. 19. Cord clamp 160 has an upper arm 161 and a lower arm 164 connected by integral hinge portion 168. Head portion 171 has a groove 178 defined by resilient flanges 179 and 180. Head portion 175 has a similar tongue configuration 177 that matingly engages groove 178 when upper and lower arms 161 and 164 are clamped together about an umbilical cord.

In the embodiment of FIGS. 16-21, upper arm 161 of clamp 160 has a protrusion 200 extending upwardly from its top surface to be matingly received in a recess 201 formed in channel 184 of upper clamping jaw 126, as shown in FIG. 20. Likewise, the lower arm 142 of blade assembly 140 has a protrusion 200 extending downwardly that mates in recess 201 formed in channel 194 of lower clamping jaw 127, as shown in FIG. 21. Eliminated in this version are the respective neck members and tongue portions of the first embodiment of the instrument and clamp of the invention.

Blade assembly 140 attaches to cord clamp 160 by a pair of pop beads 210 that mate in recesses 212 of the blade assembly.

In operation, clamp 160 and blade assembly 140 are snapped together and then loaded into surgical instrument 120. The action o closing clamping jaws 126 and 127 and thus severing the umbilical cord will either cause blade 141 to further sever pop beads 210 from lower arm 164 or wedge blade 141 between assemblies 140 and 160 so that beads 210 are pulled from engagement with recesses 212. In either event, clamp 160 and blade assembly 140 become separated when the cord clamp 160 is locked into engagement around the umbilical cord. The surgical instrument then can be removed by snapping the protrusion 200 out of recess 201.

Figure 22:
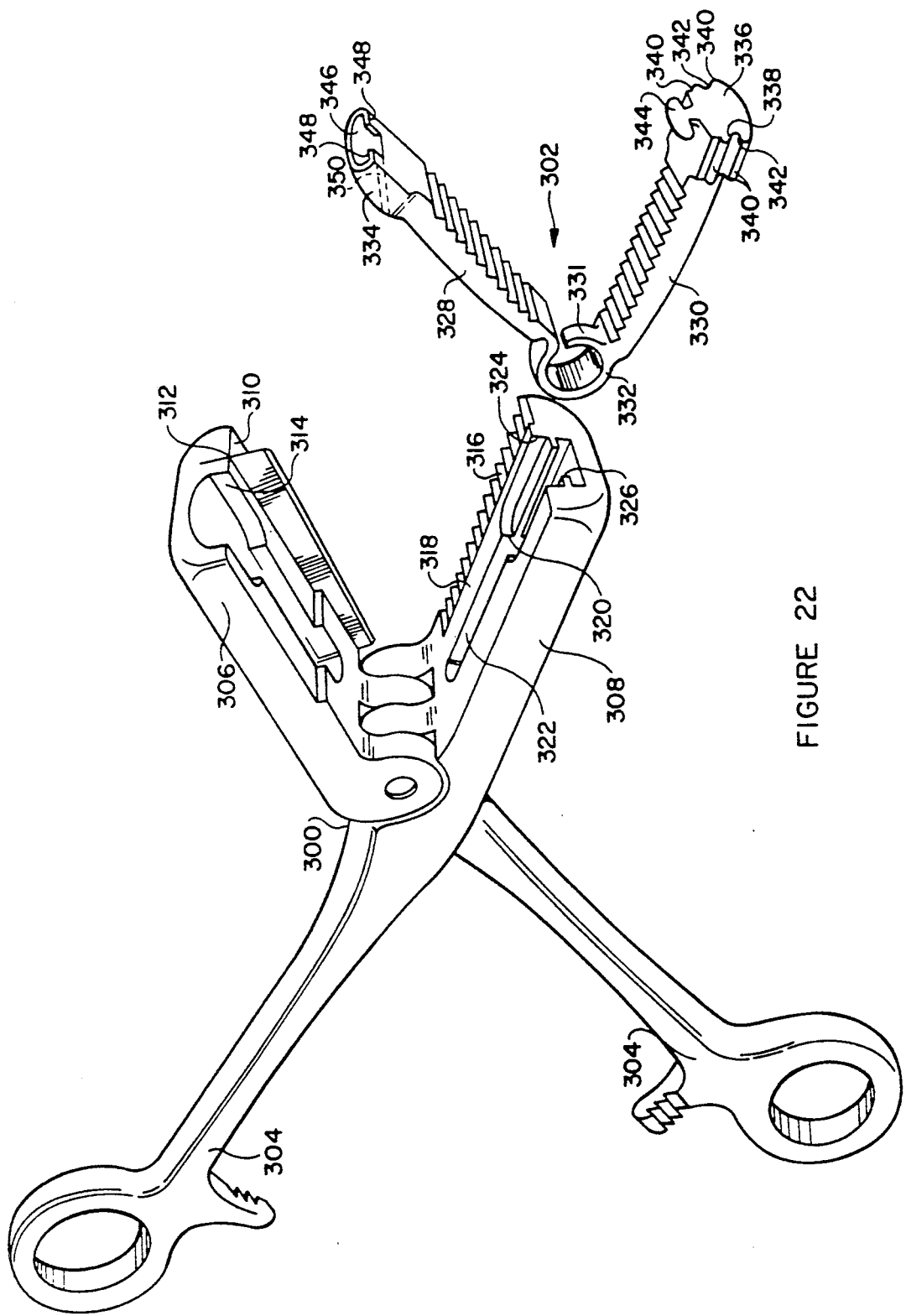
FIG. 22 is an exploded, perspective view showing a second alternative embodiment of a surgical instrument including coupling means and a clamp having corresponding coupling means for engaging the instrument in accordance with the present invention.

FIG. 22 shows in exploded view a third embodiment of a surgical instrument 300 along with a clamp 302 ideally suited for use with instrument 300, wherein different means for coupling the clamp to the instrument are utilized. Instrument 300 likewise includes scissor-like handles 304 and closing upper and lower jaws 306, 308.

Upper jaw 306 includes a hemostat surface 310 and a blade assembly 312. It is to be understood that blade assembly 312 may be either permanently or replaceably mounted on jaw 306. Upper jaw 306 further includes longitudinally extending conformed slot 314. Lower jaw 308 likewise includes a hemostat surface 316, an anvil section 318 providing a solid cutting surface for blade 312, and coupling means 320. As seen from FIGS. 22 and 23, coupling means 320 generally comprises longitudinally extending slot 322 having an enlarged forward section 324. Opposing flanges 326 extend horizontally inwardly from the side walls of forward section 324.

As shown isolated from contact with instrument 300 in FIG. 22, clamp 302 is of the V-shaped type generally having spaced apart upper and lower arms 328 and 330 which are joined together at one end by flexible hinge portion 332. Head portions 334 and 336 are respectively integrally joined with arms 328 and 330 at the free ends thereof. Clamp 302 is also provided with blocking member 331 which prevents the umbilical cord from entering the open area defined by the hinge portion 332.

Lower arm head portion 336 includes corresponding coupling means generally indicated by reference numeral 338. In particular, corresponding coupling means 338 includes a pair of longitudinal, spaced-apart ridges 340 on each side of head portion 336, to define a groove 342 therebetween.

Thus instrument 300 is adapted to slidably receive clamp 302 by sliding lower arm 330 rearwardly into slot 322 of lower jaw 308. As lower jaw 308 engages hinge 332 and lower arm 330, coupling means 320 interlocks with corresponding coupling means 338 as grooves 342 receive flanges 326. Slot 314 is configured to receive upper arm 328 and head portion 334 therein when clamp 302 is loaded into instrument 300. When so interlocked, coupling means 320 and corresponding coupling means 338 provide for sufficiently tight engagement therebetween to prevent clamp 302 from falling from instrument 300 when in use. However, means 320 and 338 do not engage so forceably as to inhibit free release of clamp 302 from instrument 300 by rearward movement of the instrument once clamping about the umbilical cord has been accomplished.

It will be appreciated that the coupling means above described with respect to the lower jaw of the instrument and the lower clamp could just as readily be placed on the upper jaw of the instrument and upper arm of the clamp, or even on both jaws and both arms, as desired.

It will be appreciated that the outer surfaces of at least one head portion of the clamp can be made of the same dimensions as the cavity 326 of the jaw shown in FIG. 22 and a horizontal groove can be formed on each side of the clamp head portion to snugly engage opposing flanges or ribs 326 so as to hold the clamp 302 with the instrument until the clamping procedure is completed, which procedure includes the simultaneous severing of the umbilical cord and the compressing of the placental end of the cord by the hemostate surfaces of the instrument. This modification obviates the need for forming the spaced-apart ridges 340 t define the grooves or indents since such grooves can be formed within the sides of the head portions of the clamps.

In still another embodiment of the clamp illustrated in FIG. 22 slot 322 which extends to the front of the instrument 300 is made deeper. Lower arm head portion 336 is provided with grooves 342 on either side thereof which initially engage ridges 326 and is further provided with a slightly larger groove formed parallel t and slightly above each of grooves 342. When the clamp 302 is placed within the instrument 300 so that grooves 342 engage ridges 326, the base of head portion 336 is spaced from the bottom of slot 322. Upon tight closure of the clamp whereby tongue 344 engages and is locked into the upper arm head portion and is held by the flanges 348, the lower arm head portion is forced downwardly into slot 322 as grooves 342 are forced past ridges 326. Ridges 326 now extend into the larger parallel grooves (not shown) directly above grooves 342. Because the ridges more loosely fit into the larger grooves, the locked clamp is more easily withdrawn from the instrument.

Alternative locking means for locking the upper and lower heads of the clamp when it is clamped about the umbilical cord are also shown in FIG. 22. These include tongue 344 integral with and extending upwardly from the end of head portion 336 and adapted to snap into recess 346 formed by resilient flanges 348 in head portion 334, which flanges spread outwardly a sufficient distance to permit tongue 344 to enter recess 346 before returning to their normal position. Of course, the tongue can be provided on the upper head and the recess on the lower head of the clamp, if desired.

Clamping and severing instrument 300 can be further modified by making hemostat surfaces 310, 316 smooth instead of serrated and fastening a semi-rigid flexible plastic strip over each of such flat surfaces, such strip surfaces having the configuration of a hemostat surface, such as serration. If desired, the strip fastened to the smooth upper hemostat surface in the upper jaw of the instrument, whose hemostat surface 310 is now shown in FIG. 22, could have a thickness of the height of the exposed blade 315 and thus simultaneously act as a guard to the blade. Alternatively, such flexible plastic hemostat strips could be secured at their ends to the instrument above the smooth surfaces (where surfaces 310 and 316 now appear) and have their body portions spaced slightly above such surfaces. In this manner, the flexible plastic strips provide a variable compliance for thick versus thin umbilical cords being severed and clamped at the placental end of the cord. The "give" of the flexible plastic strips as they are compressed about the umbilical cord would depend on the size of the cord. The flexible plastic strip on the upper clamping jaw of the instrument spaced from smooth surface 310 would also act as a guard for the blade 315. Such plastic strips could be on either or both clamping jaws of the instrument to form one or a pair of hemostat surfaces. If on one surface of the instrument, then the other clamping jaw of the instrument would be provided with hemostat surfaces 310 or 316, as shown in FIG. 22.

When it is time to remove the clamp from that portion of the umbilical cord attached to the infant, the most common procedure is to sever the clip at the hinge portion 68, 168, 332 since it is extremely difficult to separate the head portions of the clamp after they have been closed and locked. This means that clippers must always be available in order to sever the clamp at the hinge and remove it from the infant.

As illustrated in FIG. 22, the head 334 on the upper arm 328 is provided with an opening 350 extending from the upper surface of the head and communicating with the recess or cavity 346. When clamp 302 is locked and tongue 314 is disposed within recess 346 the tongue defines an axis, and, opening 350 and thus the walls 351 thereof are inclined with respect to the axis of the tongue. Tongue 314 is prevented from being withdrawn by the presence of flanges 348, a thin rigid rod or probe is inserted through the opening 350 to push against the tongue 314 in recess 346 and force the flexible tongue out of recess 346, thus disengaging the locking mechanism and separating the heads 334, 336 due to the inherent spring resiliency in the plastic structure of flexible hinge 332. The clamp is then easily removable from the umbilical cord.

FIG. 24 illustrates a modified embodiment of the clamp of FIG. 22. Head portion 334 defines the recess or cavity 346 therein bu instead of the pair of flanges 348 which lock the tongue within the recess, as shown in FIG. 22, the undersurface 352 of the head 334 is provided with a narrow neck portion 354 adapted to engage the neck portion 356 of flexible tongue 344 formed by notches 358. A pair of projections 360 (only one shown) extend vertically within recess 346. When the clamp of FIG. 24 is closed, flexible tongue 344 enters cavity 346 with the neck 356 of the tongue disposed within neck portion 354 and the tongue is held within the cavity behind the pair of projections 360. To unlock the clamp, a probe, shown generally by instrument 362, having a narrow tip portion 364, may be extended into opening 350 to release tongue 344 by pushing tongue 344 and thus notches 358 outwardly away from engagement with projections 360 in recess 346. Once tongue 344 is pushed away from contact with projections 360 by instrument 362, clamp 302 pops open due to the inherent spring resiliency in the plastic structure of flexible hinge 322.

It will be apparent that the opening 350, may be of sufficient diameter to admit any of a wide variety of medical instruments which are at hand or available to the nurse or doctor at the time the clamp is to be removed from the portion of the umbilical cord still attached to the infant. Walls 35 of the opening likewise could have varying degrees of curvature for admitting instruments having an accurate shape. The clamps according to the present invention have an opening such as exemplary opening 350 in at least one of the arms thereof; either of the arms can have such an opening in their head portions.

FIG. 25 shows still another embodiment of an umbilical clamp 500 in accordance with the present invention. Clamp 500 is also of the V-shaped variety and has rounded arms 502, 504 and rounded head portions 506 and 508. The curved or rounded configuration of clamp 500 ensures against abrading or cutting of the infant's skin after the clamp has been attached adjacent the infant's navel area.

Clamp 500 likewise includes an opening or channel 510 for permitting facilitated release of the arms of the clamp. Channel 510 opens at the top of rounded head portion 506 and has walls extending diagonally therethrough to communicate with a locking device 512 comprising recess 514 and tongue 516. Tongue 516 engages within recess 514 in any manner now well understood by those skilled in the art. Thus, upon closure of clamp 500, a similar probe (not shown) may be extended through channel 510 into recess 514 to disengage tongue 516 and thereby release clamp 500. Preferably, clamp 500 also includes corresponding coupling means (not shown) making clamp 500 suitable for use with an instrument of the type illustrated in FIG. 1.

It will also be appreciated that clamp 500 can be provided with groove 518 on either side of bottom head portion 508 for engaging the corresponding ridges 326 on instrument 300 illustrated in FIG. 22. As explained above, if slot 322 which extends to the front of the instrument 300 is made sufficiently deep then when clamp 500 is inserted therein, ridges 326 will ride in grooves 518 and the bottom of the clamp will be spaced above the bottom of the slot. By applying closing pressure on the clamp by the instrument tongue 516 will enter recess 514 and be locked therein while simultaneously applying sufficient pressure to the bottom clamp head 508 to force the ridges 326 upwardly out of the groove 518 and into either a larger groove (not shown) directly above and parallel to each of grooves 518, or into the space above the groove 518 and its laterally extending ledge or ridge portion 520, so as to more readily facilitate removal of the closed clamp from the instrument 300.

Although the present invention has been described with reference to preferred embodiments, other modifications and arrangements could be made within the scope of the disclosed invention.

What is claimed is:

1. An umbilical cord clamp applicable by compressive force, said clamp being formed of a flexible material and comprising:
   a first arm;
   a second arm connected at one end to the first arm with the free ends of said arms being normally spaced apart from movable toward each other by the compressive force; and
   means on said free ends for releasably locking said ends together in clamping position, said locking means including, on one arm, flexible tongue means extending along an axis and means on the other of said arms for releasably engaging said tongue means when said tongue means is received within a recess of said other arm,
   at least one of said arms having an opening extending from the outer surface thereof to said recess and said flexible tongue means when said clamp is closed,
   at least a portion of the walls of said opening being inclined with respect to said axis when said clamp is closed to adapt said opening for receiving and guiding a probe to push said tongue means to flex out of engagement with said engaging means and unlock said arms.

2. An umbilical cord clamp as claimed in claim 1, wherein said engaging means comprises flanges.

3. An umbilical cord clamp as claimed in claim 2, wherein said opening opens at said outersurface behind said tongue means to direct the probe to push said tongue means forwardly out of engagement with said flanges.

4. An umbilical cord clamp as claimed in claim 2, wherein said engaging means further comprises projections extending vertically within said recess.

5. An umbilical cord clamp as claimed in claim 4, wherein said opening opens at said outersurface behind said tongue means to direct the probe to push said tongue means forwardly out of engagement with said projections.

6. An umbilical cord clamp as claimed in claim 1, wherein said arms are rounded.

7. An umbilical cord clamp applicable by compressive force exerted by the jaws of a scissor-like surgical instrument, said clamp being formed of a flexible material and comprising:
   a first arm;
   a second arm connected at one end to the first arm with the free ends of said arms being normally spaced apart, said free ends each having a head portion thereon which is remote from the connection between the arms;
   means on opposite sides of said head portion of at least one of said arms for releasably coupling said clamp to the surgical instrument, said coupling means including a first ridge inparallel, spaced apart relation with a second ridge thereon to define a groove therebetween; and
   means on said arms for locking said free ends together in clamping position whereby the compressive force moves said free ends toward each other whereupon said locking means locks said free ends together, said locking means including, on one arm, flexible tongue means extending along an axis and means on the other of said arms for releasably engaging said tongue means when said tongue means is received within a recess of said other arm, one of said arms having an opening extending from the outer surface thereof to said flexible tongue means, at least a portion of the walls of said opening being inclined with respect to said axis when said clamp is closed to adapt said opening for receiving and guiding a probe to push said tongue means to flex out of engagement with said engaging means and unlock said arms.

8. An umbilical cord clamp as claimed in claim 7, wherein said arms are rounded.

9. An umbilical cord clamp applicable by compressive force exerted by the jaws of a scissor-like surgical instrument, said clamp being formed of a flexible material and comprising:

a first arm;

a second arm connected at one end to the first arm with the free ends of said arms being normally spaced apart;

means on at least one of said arms for releasably coupling said clamp to the surgical instrument said coupling means on said at least one arm having a primary groove with substantially the same dimensions as a tongue portion on at least one of the jaws of the surgical instrument and a secondary groove with dimensions larger than the tongue portion, said primary groove receiving the tongue portion to nondisengageably connect said clamp and the surgical instrument, the compressive force forcing the tongue portion into said secondary groove to disengageably connect said clamp and the instrument; and means on said arm for locking said free ends together in clamping position.

10. An umbilical cord clamp as claimed in claim 21, wherein said locking means includes, on one arm, flexible tongue means extending along an axis and means on the other of said arms for releasably engaging said tongue means when said tongue means is received within a recess of said other arm, one of said arms having an opening extending from the outer surface thereof to said flexible tongue means, at least a portion of the walls of said opening being inclined with respect to said axis when said clamp is closed whereby said opening is adapted for guiding a probe to push said tongue means, said tongue means flexing out of engagement with said engaging means in said recess when a probe guided by said wall portion is pushed thereagainst.

11. An umbilical cord clamp assembly applicable by compressive force exerted by the jaws of a scissor-like surgical instrument, said assembly comprising a cord clamp formed of a flexible material and a blade means, said clamp comprising:

a first arm, a second arm connected at one end to the first arm with the free ends of said arms being normally spaced apart, first means on an arm of said clamp of releasably coupling said clamp to said blade means, said first means comprising at least one bead member extending outwardly from a side of said arm, second means on an arm of said clamp for releasably coupling said clamp to the surgical instrument, and means on said arms of said clamp for locking said free ends thereof together in clamping position under compressive forces, said locking means on said arms of said clamp including, on one arm, flexible tongue means extending along an axis and means on the other of said arms for releasably engaging said tongue means when said tongue means is received in a recess of said other arm, one of said arms having an opening extending from the outer surface thereof to said recess and said flexible tongue means when said clamp is closed, at least a portion of the walls of said opening being inclined with respect to said axis when said clamp is closed to adapt said opening for guiding a probe to push said tongue means to flex out of engagement with said engaging means and unlock said arms; and said blade means comprising a first arm having a receptacle for receiving said bead member to couple said clamp and said blade means in side-by-side relation, a second arm connected to one end of said first blade means arm, a blade positioned on said second blade means arm to move between said first blade means arm and said side of said clamp arm having said bead member to disconnect said clamp from said blade means upon closure of said arms of said clamp.

* * * * *